United States Patent
Deshayes et al.

(10) Patent No.: US 10,702,458 B2
(45) Date of Patent: *Jul. 7, 2020

(54) COMPOSITIONS COMPRISING MICROPIGMENTS

(71) Applicant: DSM IP ASSETS B.V., Heerlen (NL)

(72) Inventors: Cyrille Deshayes, Kaiseraugst (CH);
Andre Duesterloh, Kaiseraugst (CH);
Anne Janssen, Kaiseraugst (CH);
Thomas Rudolph, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/312,593

(22) PCT Filed: Jun. 27, 2017

(86) PCT No.: PCT/EP2017/065892
§ 371 (c)(1),
(2) Date: Dec. 21, 2018

(87) PCT Pub. No.: WO2018/002074
PCT Pub. Date: Jan. 4, 2018

(65) Prior Publication Data
US 2019/0254940 A1 Aug. 22, 2019

(30) Foreign Application Priority Data
Jun. 27, 2016 (EP) .................................. 16176423

(51) Int. Cl.
| | |
|---|---|
| *A61K 8/06* | (2006.01) |
| *A61K 8/25* | (2006.01) |
| *A61K 8/29* | (2006.01) |
| *A61K 8/34* | (2006.01) |
| *A61K 8/55* | (2006.01) |
| *A61Q 1/10* | (2006.01) |
| *A61Q 1/12* | (2006.01) |
| *A61Q 17/04* | (2006.01) |
| *A61Q 19/04* | (2006.01) |

(52) U.S. Cl.
CPC ............... *A61K 8/062* (2013.01); *A61K 8/25* (2013.01); *A61K 8/29* (2013.01); *A61K 8/342* (2013.01); *A61K 8/55* (2013.01); *A61Q 1/10* (2013.01); *A61Q 1/12* (2013.01); *A61Q 17/04* (2013.01); *A61Q 19/04* (2013.01); *A61K 2800/412* (2013.01); *A61K 2800/413* (2013.01); *A61K 2800/43* (2013.01); *A61K 2800/596* (2013.01); *A61K 2800/621* (2013.01); *A61K 2800/623* (2013.01)

(58) Field of Classification Search
CPC . A61K 8/062; A61K 8/25; A61K 8/29; A61K 8/342; A61K 8/55; A61K 2800/412; A61K 2800/413; A61K 2800/43; A61K 2800/596; A61K 2800/621; A61K 2800/623; A61Q 1/10; A61Q 17/04
See application file for complete search history.

(56) References Cited

U.S. PATENT DOCUMENTS

| | | |
|---|---|---|
| 5,559,089 A | 9/1996 | Hartman et al. |
| 2011/0142772 A1* | 6/2011 | Janssen .................. A61K 8/35 424/60 |
| 2012/0258055 A1* | 10/2012 | Gray .................... A61K 8/26 424/59 |
| 2014/0178318 A1* | 6/2014 | Janssen .................. A61K 8/86 424/60 |

FOREIGN PATENT DOCUMENTS

WO 01/62375 8/2001

OTHER PUBLICATIONS

Croda,: "Croda Europe Ltd Cowick Hall Smith Goole East," Sep. 1, 2014.*
International Search Report for PCT/EP2017/065892, dated Aug. 16, 2017, 3 pages.
Croda,: "Croda Europe Ltd Cowick Hall Snaith Goole East", Sep. 1, 2014, 9 pages.
DSM: "Product Information Product Data Sheet—Amphisol® A", May 23, 2011, 2 pages.
DSM: "Product Information Product Data Sheet—Amphisol® K", Jun. 16, 2015, 3 pages.

\* cited by examiner

*Primary Examiner* — Blessing M Fubara
(74) *Attorney, Agent, or Firm* — Nixon & Vanderhye P.C.

(57) ABSTRACT

The present invention relates to topical compositions comprising at least one inorganic micropigment and a cetyl phosphate surfactant mixture consisting essentially of mono- and/or dicetyl esters of phosphoric acid or salts thereof and cetylalcohol and inorganic phosphate and heavy metals and water, characterized in that the surfactant mixture contains no organochlorine impurities and has an inorganic phosphate content of less than 0.7 wt.-% and a heavy metal content of less than 12 ppm.

16 Claims, No Drawings

COMPOSITIONS COMPRISING MICROPIGMENTS

This application is the U.S. national phase of International Application No. PCT/EP2017/065892 filed 27 Jun. 2017, which designated the U.S. and claims priority to EP Patent Application No. 16176423.8 filed 27 Jun. 2016, the entire contents of each of which are hereby incorporated by reference.

The present invention relates to topical compositions comprising at least one inorganic micropigment and a cetyl phosphate surfactant mixture consisting essentially of mono- and/or dicetyl esters of phosphoric acid or salts thereof and cetylalcohol and inorganic phosphate and heavy metals and water, characterized in that the surfactant mixture contains no organochlorine impurities and has an inorganic phosphate content of less than 0.7 wt.-% and a heavy metal content of less than 12 ppm.

'Cetyl phosphates', consisting essentially of mono- and/or dicetyl phosphate, cetyl alcohol and inorganic phosphate in varying amounts are widely used as surfactants in the cosmetic industry and are sold under the INCI Cetyl phosphate. The combination of such cetyl phosphates and inorganic micropigments is widely used in the cosmetic industry such as e.g. in sunscreen formulations but also in color cosmetic applications such as in mascara formulations or foundation/make-up compositions. The synthesis of highly effective cetyl phosphates from cetyl alcohol and phosphorous oxy chloride has been known for a long time. Such cetyl phosphates are e.g. commercially available under the Amphisol® brand at DSM Nutritional Products Ltd. This route however is getting less attractive because of the unavoidable formation of organochlorine impurities, such as in particular cetyl chloride. Thus, recently several chlorine-free cetyl phosphates have been brought to the market, which, however, exhibit formulation issues, in particular when formulating compositions comprising in addition at least one inorganic micropigment.

Thus, there is an ongoing need for a chlorine-free cetyl phosphate, i.e. a cetyl phosphate not containing organochlorine impurities such as in particular cetyl chloride, which allows the formulation of compositions comprising an inorganic micropigment without negatively effecting the viscosity. Such a cetyl phosphate should furthermore be obtainable in a sustainable and economical way avoiding e.g. the use of aromatic or halogenated solvents.

Surprisingly it has been found, that a specific chlorine-free cetyl phosphate which has an inorganic phosphate content of less than 0.7 wt.-% and a heavy metal content of less than 12 ppm allows the formulation of topical compositions comprising an inorganic micropigment within an acceptable viscosity range.

Thus, in a first embodiment, the present invention relates to topical compositions comprising at least one inorganic micropigment and a cetyl phosphate surfactant mixture consisting essentially of mono- and/or dicetyl esters of phosphoric acid or the respective salts thereof and cetylalcohol and inorganic phosphate and heavy metals and water, characterized in that the surfactant mixture contains no organochlorine impurities and has an inorganic phosphate content of less than 0.7 wt.-% and a heavy metal content of less than 12 ppm.

In particular the topical compositions contain the cetyl phosphate surfactant mixture as sole surfactant.

The term 'cetyl phosphate' as used herein refers to a mixture consisting essentially of mono- and/or dicetyl phosphate, cetylalcohol, inorganic phosphate, heavy metals, and residual water. Such surfactant mixtures are sold under the INCI name 'cetyl phosphate'.

The cetyl phosphate can be used in its free acid form, preferably however in all embodiments of the present invention, the cetyl phosphate is used as a salt with a cosmetically acceptable cation e.g. as diethanolamine or potassium salt, most preferably as potassium salt (i.e. as potassium cetyl phosphate).

Consequently, the term 'cetyl phosphate surfactant mixture' as used herein refers to a mixture consisting essentially of mono- and/or F and/or dicetyl phosphate (i.e. mono- and/or dicetyl esters of phosphoric acid or the respective salts thereof), cetylalcohol, inorganic phosphate, heavy metals and residual water.

The term 'inorganic phosphate' refers to the total amount of free phosphate ($PO_4^{3-}$) in the cetyl phosphate surfactant mixture as determined by means of the IC method. In a preferred embodiment, the total amount of the inorganic phosphate is less than 0.5 wt.-%, based on the total weight of the cetyl phosphate surfactant mixture. Consequently, it is well understood by a person skilled in the art, that the inorganic phosphate content in the topical compositions is accordingly preferably less than 0.05 wt.-%, based on the total weight of the topical composition.

The term 'heavy metal content' refers to the total amount of chromium, iron, antimony, arsenic, nickel and aluminum. The total amount of chromium, iron, antimony, arsenic, nickel and aluminum present in the cetyl phosphate surfactant mixture is determined by means of ICP-OES (e.g. at Solvias, Eurofins). In a preferred embodiment, the total amount of arsenic and aluminum in the cetyl phosphate surfactant mixtures according to the invention is, independently of each other, below 2 ppm, more preferably below 1 ppm.

The cetyl phosphate surfactant mixture can be used in its free acid form, i.e. containing mono- and/or dicetyl esters of phosphoric acid. Preferably however in all embodiments of the present invention, the cetyl phosphate surfactant mixture is used as a salt with a cosmetically acceptable cation e.g. as diethanolamine or potassium salt, most preferably as potassium salt (i.e. as potassium cetyl phosphate surfactant mixture i.e. containing the respective potassium salts of the mono- and/or dicetyl esters of phosphoric acid).

The amount of the cetyl phosphate surfactant mixture in the topical composition according to the present invention is typically selected in the range of 0.1 to 10 wt.-%, more preferably in the range of 0.3 to 8 wt.-%, most preferably in the range of 0.5 to 8 wt.-%, based on the total weight of the topical composition.

Based on the above mentioned preferred amounts of the cetyl phosphate surfactant mixture, it is well understood to a person skilled in the art, that the topical compositions according to the present invention accordingly comprise preferably an amount of inorganic phosphate selected in the range of 0.0007 to 0.07 wt.-%, more preferably in the range of 0.0021 to 0.035 wt.-%, most preferably in the range of 0.0035 to 0.021 wt.-%, based on the total weight of the topical composition. Even more preferably, the inorganic phosphate content in the topical compositions according to the present invention is less than 0.01 wt.-% as this results in particularly stable compositions.

The total amount of the at least one inorganic micropigment is typically selected in the range of 0.1 wt.-% to 40 wt.-%, preferably in the range of 0.5 wt.-% to 20 wt.-%, more preferably in the range of 1 wt.-% to 10 wt.-% and most preferably as in the range of 5 to 10 wt.-%, based on the total weight of the topical composition.

In all embodiments according to the present invention, the cetyl phosphate surfactant mixture preferably consists essentially of 60-95 wt.-% of monocetyl phosphoric acid or a salt thereof, 0-15 wt.-% of dicetyl phosphoric acid or a salt thereof, 0-20 wt.-% of cetyl alcohol, 0-0.7 wt.-% of inorganic phosphate, 0-12 ppm of heavy metals and 0-4 wt.-% of residual water. More preferably, the cetyl phosphate surfactant mixture consists essentially of 70-90 wt.-% of monocetyl phosphoric acid or a salt thereof, 0.5-12 wt.-% of dicetyl phosphoric acid or a salt thereof, 0-15 wt.-% of cetyl alcohol, 0-0.7 wt.-% of inorganic phosphate, 0-12 ppm of heavy metals and 0-3 wt.-% of residual water. Most preferably the cetyl phosphate according to the present invention consists essentially of 70-85 wt.-% of monocetyl phosphoric acid or a salt thereof, 5-10 wt.-% of dicetyl phosphoric acid or a salt thereof, 7-12 wt.-% of cetyl alcohol, 0-0.5 wt.-% of inorganic phosphate, 0-11 ppm of heavy metals and 0-3 wt.-% of residual water.

Most preferably in all embodiments of the present invention the cetyl phosphate surfactant mixture is a potassium cetyl phosphate surfactant mixture consisting essentially of 72-85 wt.-% of monocetyl phosphate, 0.5-10 wt.-% of dicetyl phosphate, 0-15 wt.-% of cetyl alcohol, 7-12 wt.-% of potassium, 0-0.6 wt.-% of inorganic phosphate, 0-11 ppm of heavy metals and 0-2.5 wt.-% of residual water, even more preferably of 72-80 wt.-% of monocetyl phosphate, 5-10 wt.-% of dicetyl phosphate, 7-12 wt.-% of cetyl alcohol, 7-12 wt.-% of potassium, 0-0.5 wt.-% of inorganic phosphate, 0-10 ppm of heavy metals and 0-2.5 wt.-% of residual water.

The term 'consisting essentially of' as used according to the present invention means that the total amount of the listed ingredients ideally sums up to 100 wt.-%. It is however not excluded that small amount of impurities derived from the production process may be present.

In another preferred embodiment of the present invention, the ratio (w/w) of mono- and/or dicetyl esters of phosphoric acid or salts thereof in the cetyl phosphate surfactant mixture according to the present invention is selected in the range of 170 to 1, preferably in the range of 20 to 5, most preferably in the range of 15 to 8.

The residual water content is to be understood as determined by Karl Fischer titration (e.g. described in Eugen Scholz Karl-Fischer-Titration, Springer-Verlag 1984 or the WHO Method WHO/M/7.R1).

The term 'chlorine-free' as used herein refers to a cetyl phosphate surfactant mixture which is substantially free (i.e. below limit of detection) of organochlorine impurities such as in particular of cetyl chloride. In a preferred embodiment, the term 'chlorine-free' refers to a cetyl phosphate surfactant mixture prepared via a route not employing any phosphorous oxy chloride, halogenated reagents or halogenated solvents, by which means the formation of organochlorine impurities such as in particular cetyl chloride is per se avoided.

Thus, preferred in all embodiment according to the present invention is a cetyl phosphate surfactant mixture prepared by reacting cetyl alcohol with pyrophosphoric acid in hexane and/or cyclohexane, preferably cyclohexane, at a reaction temperature of about 60 to 90° C., preferably 70 to 85° C. followed by hydrolysis with water resulting in the respective mixture of mono- and/or dicetyl esters of phosphoric acid, cetyl alcohol, inorganic phosphate, heavy metals and residual water.

Thus, the present invention relates to a process for the preparation of a cetyl phosphate surfactant mixture consisting essentially of mono- and/or dicetyl esters of phosphoric acid or salts thereof and cetylalcohol and inorganic phosphate and heavy metals and water, said process comprising the steps of (i) reacting cetyl alcohol with pyrophosphoric acid in hexane and/or cyclohexane at 60 to 90° C., followed by (ii) hydrolysis of the resulting reaction mixture with water in order to obtain the cetyl phosphate surfactant mixture and optionally (iii) treating the cetyl phosphate obtained in step (ii) with potassium hydroxide to obtain the respective potassium salt of the cetyl phosphate surfactant mixture.

The ratio (mol) of pyrophosphoric acid to cetyl alcohol is preferably selected in the range of 5 to 1, more preferably in the range of 4 to 2, most preferably in the range of 3.5 to 2.5.

The respective salts are prepared by standard methods in the art e.g. by reacting the free acid with a base releasing a cosmetically acceptable cation such as e.g. with an aqueous solution of potassium hydroxide.

The present invention accordingly also relates to cetyl phosphate surfactant mixtures obtained by the process according to the present invention.

A particular suitable cetyl phosphate surfactant mixture according to the present invention is commercially available as Amphisol® L at DSM Nutritional products Ltd.

As the specific cetyl phosphate surfactant mixture as well as the respective salts thereof according to the present invention are still novel, the present invention also relates to a cetyl phosphate surfactant mixture consisting essentially of mono- and/or dicetyl esters of phosphoric acid or salts thereof and cetylalcohol and inorganic phosphate and heavy metals and water, characterized in that the surfactant mixture contains no organochlorine impurities and has an inorganic phosphate content of less than 0.7 wt.-% and a heavy metal content of less than 12 ppm.

Particularly suitable inorganic micropigments in all embodiments of the present invention are metal powders, metal oxides or metal hydroxides conventionally used in cosmetic applications either as inorganic sunscreening agent or as colouring agent. Exemplary inorganic micropigments according to the present invention encompass magnesium oxide, magnesium hydroxide, calcium oxide, calcium hydroxides, aluminum oxide, aluminum hydroxide, iron oxides ($\alpha$-$Fe_2O_3$, $\gamma$-$Fe_2O_3$, $Fe_3O_4$, FeO), red iron oxide, yellow iron oxide, black iron oxide, iron hydroxides, titanium (di)oxides, zirconium oxides, chromium oxides, chromium hydroxides, manganese oxides, cobalt oxides, cerium oxides, nickel oxides and zinc oxides as well as composite oxides and composite hydroxides such as iron titanate, cobalt titanate and cobalt aluminate.

The inorganic micropigments according to the present invention may optionally be surface treated to, for example, make the particles more hydrophobic or more dispersible in a vehicle.

Particularly preferred inorganic micropigments according to the present invention are selected from the group consisting of titanium dioxides, zinc oxides and iron oxides, most preferably from titanium dioxide and iron oxide, as well as mixtures thereof.

In one particular advantageous embodiment the inorganic micropigment is an inorganic sunscreening agent having a particle size which is principally useful for incorporation into a sunscreen composition such as in particular a titanium dioxide or zinc oxide sunscreening agent.

These inorganic sunscreening agents are preferably used in an amount (total) selected in the range of 0.1 wt.-% to 20 wt.-%, preferably in the range of 0.5 wt.-% to 10 wt.-%, more preferably in the range of 1 wt.-% to 10 wt.-%, based on the total weight of the topical composition.

Preferably, in all embodiments of the present invention, a titanium dioxide sunscreening agent having an average primary particle size of about 2 nm to 100 nm, preferably of about 5 to 50 nm and a secondary particle size of about 0.05 to 50 μm, preferably of about 0.1 to 1 μm is used.

The crystalline form of the titanium dioxide sunscreening agent may be of any crystal or amorphous type. For example, titanium dioxide may be any type of amorphous, rutil, anastase, brookite or a mixture thereof.

In a preferred embodiment, the titanium dioxide sunscreening agent used according to the present invention is coated with an organic coating such as e.g. selected from polyols, methicone, or alkyl silane. Such coatings are well known in the art. Commercially available organic coated titanium dioxides suitable according to the invention are e.g. available as Uvinul® TiO₂ by BASF or Eusolex® T-Avo by Merck.

In a particular preferred embodiment, the titanium dioxide sunscreening agent is coated with an organic coating selected from silica, silicone oils (e.g. simethicones, methicones, dimethicones, polysilicone-15) or alkyl silanes. Commercially available organic coated titanium dioxides particularly suitable according to the invention are e.g. available as Uvinul® TiO₂ (INCI: trimethoxycaprylylsilane and titanium dioxide ex BASF) or Eusolex® T-Avo (INCI: Titanium dioxide, Silica ex Merck).

In another advantageous embodiment the titanium dioxide sunscreening agent is a non-coated titanium dioxide suitable for cosmetic applications such as pyrogenic titanium dioxide (e.g. AEROXIDE P25 ex Degussa).

In a more particular embodiment of the invention, the titanium dioxide sunscreening agent is a double coated titanium dioxide having an inner inorganic silica coating and an outer organic coating (referred to as double coated titanium dioxide). Such coated titanium dioxides nanoparticles can be prepared according to the state of the art or are commercially available as PARSOL® TX (INCI: Titanium Dioxide, Silica, Dimethicone ex DSM Nutritional Products) or as UV-Titan X195 (coated with silica and treated with a silicone oil (i.e. methicone) ex Kemira).

The inner coating of the titanium dioxide particle with inorganic silica can be prepared according to the state of the art as e.g. described in EP-A 988 853, EP-A 1 284 277, EP0988853, and U.S. Pat. No. 5,562,897, JP 2000319128.

The inner coating layer consists of minimum 0.5 wt %. Preferably 0.5-50 wt. % inorganic silica (based on titanium dioxide), most preferably of 1-20 wt. %. The outer coating can be selected from the class of organic coatings such as organic polymers e.g. silicone oils (e.g. simethicones, methicones, dimethicones, polysilicone-15), alkyl silanes, olefinic acids such as stearic acid or polyols such as glycerol or organophosphonic acids. The outer coating layer consists of minimum 0.25 wt. % based on titanium dioxide. Preferably of 0.5-50 wt. %, most preferably of 0.5-10 wt. %.

Other usual organic coatings can additionally be present in order to yield multiple coated (such as e.g. triple coated) titanium dioxide. The other coatings can be applied before, after or together with the second outer coating. Other additional coatings which can be used comprise organic coatings such as stearic acid, silicones (silane derivatives such as triethoxycaprylylsilane or siloxane derivatives such as methicone, dimethicone, simethicone).

In all embodiments of the present invention the titanium dioxide sunscreening agent is most preferably a double coated titanium dioxide (having an inner inorganic silica coating) wherein the outer coating consists of simethicone, methicone, dimethicone (also known as polydimethylsiloxane), polysilicone-15, stearic acid, glycerol and mixtures thereof, in particular of methicone, dimethicone, stearic acid or mixtures thereof. Most preferably, the outer coating consists of methicone or dimethicone, in particular of dimethicone is. Most preferred according to the invention the titanium dioxide sunscreening agent is UV-Titan X195 by Kemira and/or PARSOL® TX by DSM Nutritional products which are titanium dioxide grades coated with silica (inner coating) and treated with a silicone oil such as in particular methicone (UV-Titan X195) or dimethicone (PARSOL® TX) as outer coating. Most in particular PARSOL® TX by DSM Nutritional products is used as titanium dioxide sunscreening agent in the compositions according to the invention.

In another advantageous embodiment, the inorganic micropigment is a coloring agent conventionally used in decorative cosmetics such as mascara, make-up and foundation compositions. Particularly suitable inorganic coloring agents according to the present invention are titanium dioxide, zirconium or cerium oxides, zinc, iron (black, yellow or red) or chromium oxides, manganese violet, ultramarine blue, chromium hydrate and ferric blue, or metal powders, such as aluminium powder or copper powder.

These inorganic coloring agents are preferably used in an amount (total) selected in the range of 1 wt.-% to 40 wt.-%, preferably in the range of 2 wt.-% to 30 wt.-%, more preferably in the range of 5 wt.-% to 15 wt.-%, based on the total weight of the topical composition.

Preferably, in all embodiments of the present invention, an inorganic coloring agent selected from the group consisting of iron oxide and titanium dioxide which has a particle size ranging from about 0.001 to 150 μm, preferably from about 0.002 to 100 μm, more preferably from about 0.02 to 50 μm is used. Such inorganic coloring agents are well known to a person skilled in the art and e.g. commercially available under the tradename UNIPURE at Sensient.

The crystalline form of the iron and titanium dioxide coloring agent may be of any crystal or amorphous type suitable for that purpose. For example, titanium dioxide may be any type of amorphous, rutil, anastase, brookite or a mixture thereof. The particle shape of the iron oxide coloring agent may be of any acicular, spheroidal or cubic shape, as well as mixtures thereof.

In a preferred embodiment, the iron oxide and titanium dioxide coloring agents used according to the present invention are surface treated with an organic coating such as with an alkylsilane e.g. triethoxycaprylylsilane, with a silicone oil e.g. dimethicone or methicone, with an organo titanate, and/or with natural surface treatments e.g. polyhydroxystearic acid, stearoyl glutamic acid hydrogenated lecithin, jojoba esters and sodium glycerophosphate. Such coated inorganic coloring agents are well known to a person skilled in the art and e.g. commercially available under the tradename UNIPURE at Sensient, or from the product portfolio for coloring agents at KOBO, Merck.

The compositions according to the invention are intended for topical application, which is to be understood as the external application to keratinous substances, such as in particular the skin or the hair.

As the compositions according to the invention are intended for topical application, they comprise a physiologically acceptable medium, that is to say a medium compatible with keratinous substances, such as the skin, mucous membranes, and keratinous fibers. In particular the physiologically acceptable medium is a cosmetically acceptable carrier.

The term 'cosmetically acceptable carrier' as used herein refers to a physiologically acceptable medium which is compatible with keratinous substances. Suitable carriers are well known in the art and are selected based on the end-use application. Preferably, the carriers of the present invention are suitable for application to skin (e.g. in the form of creams, milks, lotions, masks, serums, hydrodispersions, foundations, creamgels, or gels etc.) or hair such as in particular eyelashes or eyebrows (e.g. mascara). Such carriers are well-known to one of ordinary skill in the art and can include one or more compatible liquid or solid filler diluent, excipient, additive or vehicle which are suitable for application to skin and/or hair.

Examples of cosmetic excipients, diluents, adjuvants, additives as well as active ingredients commonly used in the skin care industry which are suitable for use in the cosmetic compositions of the present invention are for example described in the International Cosmetic Ingredient Dictionary & Handbook by Personal Care Product Council (http://www.personalcarecouncil.org/), accessible by the online INFO BASE (http://online.personalcarecouncil.org/jsp/Home.jsp), without being limited thereto.

Particularly suitable excipients, diluents, adjuvants additives for the compositions according to the present invention are cosmetic oils such as C12-15 alkyl benzoate, cetyl alcohol, cetearyl alcohol, capric/caprylic triglycerides, diisopropylsebacate, preservatives such as phenoxyethanol and ethlyhexylglycerin (Euxyl PE 9010 from Shülke& Mayr), parabens (Euxyl K 300 form Schülke&Mayr); thickening agents for the aqueous phase such as polysaccharide such as e.g. Xanthan Gum (Keltrol CGT from Kelco); biopolymers such as e.g. cellulose gum (Tylose CG 200 from SE Tylose); mineral thickeners such as e.g. magnesium aluminium silicate (Veegum from Vanderbilt), synthetic polymers such as e.g. carbomer (Carbopol 980 from Lubrizol), UV-filters, fragrances as well as humectants such as e.g. glycerin and propylene glycol.

In accordance with the present invention, the compositions according to the invention may also comprise further cosmetically active ingredients conventionally used in cosmetic compositions. Exemplary active ingredients encompass skin lightening agents, UV-filters, agents for the treatment of hyperpigmentation, agents for the prevention or reduction of inflammation, firming, moisturizing, soothing and/or energizing agents as well as agents to improve elasticity and skin barrier.

The necessary amounts of the active ingredients as well as the excipients, diluents, adjuvants, additives etc. can, based on the desired product form and application, easily be determined by the skilled person. The additional ingredients can either be added to the oily phase, the aqueous phase or separately as deemed appropriate.

The cosmetically active ingredients useful herein can in some instances provide more than one benefit or operate via more than one mode of action.

Of course, one skilled in this art will take care to select the above mentioned optional additional ingredients, adjuvants, diluents and additives and/or their amounts such that the advantageous properties intrinsically associated with the combination in accordance with the invention are not, or not substantially, detrimentally affected by the envisaged addition or additions.

The topical compositions according to the present invention are typically prepared by admixing the cetyl phosphate surfactant mixture according to the present invention and the inorganic micropigment with suitable excipients, diluents, adjuvants and/or additives. If desired, active ingredients can additionally be added to the topical compositions according to the present invention.

Thus, the invention also relates to a process for the preparation of a topical composition according to the present invention, said process comprising the step of admixing a cetyl phosphate surfactant mixture and at least one inorganic micropigment according to the present invention with a cosmetically acceptable carrier.

In a particularly preferred embodiment, the topical compositions according to the present invention are sunscreen compositions for the protection of the skin against harmful UV-radiation, make-up and/or foundation compositions for the provision of a uniform "base" skin color or mascara compositions for coloring and/or elongation of eyelashes.

The sunscreen compositions according to the present invention preferably exhibit a viscosity selected in the range of 1,000 to 40,000, more preferably in the range of 2,000 to 30,000 mPas, most preferably in the range of 3,000 to 20,000 mPas.

The mascara compositions according to the present invention preferably exhibit a viscosity selected in the range of 20,000 to 50,000, more preferably in the range of 30,000 to 40,000 mPas. The make-up/foundation compositions according to the present invention preferably exhibit a viscosity selected in the range of 10,000 to 40,000, more preferably in the range of 20,000 to 40,000 mPas.

The compositions according to the present invention preferably are in the form of an emulsion or micro emulsion (in particular of oil-in-water (O/W) or water-in-oil (W/O) type, silicone-in-water (Si/W) or water-in-silicone (W/Si) type, PIT-emulsion, multiple emulsion (e.g. oil-in-water-in oil (O/W/O) or water-in-oil-in-water (W/O/W) type), pickering emulsion, hydrogel, alcoholic gel, lipogel, one- or multiphase solution or vesicular dispersion or other usual forms, which can also be applied by pens, as masks or as sprays.

In a particular advantageous embodiment, the compositions according to the present invention are in the form of an oil-in-water (O/W) emulsion comprising an oily (waxy) phase dispersed in an aqueous phase in the presence of a cetyl phosphate surfactant mixture according to the present invention. The preparation of such O/W emulsions is well known to a person skilled in the art. The amount of oily (waxy) phase in such O/W emulsions is preferably at least 10 wt.-%, more preferably in the range of 10 to 60 wt.-%, most preferably in the range of 15 to 50 wt.-%, such as in the range of 15 to 40 wt.-%.

The O/W emulsions according to the present invention may contain further surfactants typically employed in O/W emulsions such as e.g. Glyceryl Sterate Citrate (Imwitor 372 form Oleo GmbH), polymeric emulsifiers such as e.g. Stereath-2 (Brij 72 from Croda) or Laureth-23 (Brij-35 from Croda) as well as nonionic emulsifiers such as e.g. Glyceryl Stearate SE (Tegin M Peletts from Evonik).

O/W emulsion suitable for mascara compositions typically contain emulsified waxes, pasty fatty substances, gums and/or polymers with pigments dispersed into the water or oil (waxy) phase. Thus, in an advantageous embodiment, the mascara compositions according to the present invention comprises at least one wax, pasty fatty substance, gum or polymer in an amount selected in the range of 0.5 to 30 wt.-%, preferably in the range of 10 to 25 wt.-% based on the total weight of the composition.

Particularly suitable waxes, pasty fatty substances, gums and polymers for the mascara compositions according to the present invention encompass natural waxes such as beeswax, carnauba or candelilla wax; paraffin wax; ceresin or ozokerite; synthetic waxes such as polyethylene or silicone waxes (e.g. alkyl or alkoxy dimethicones), microcrystalline waxes (e.g. Multiwax W-44 (Sonneborn)); triglycerides (e.g. capric/caprlyic triglycerides (Myritol 312 (BASF)) and castor oil); hydrocarbons such as liquid paraffin, petrolatum and squalane (e.g. Fitoderm (BASF)); fatty acids such as stearic acid and palmitic acid (e.g. Cutina FS-45 (BASF)); higher alcohols such as cetearyl Alcohol (Lanette 0 (BASF)) and stearyl alcohol (Lanette 18 (BASF)); and ester oils (e.g. cetyl 2-ethylhexanoate (CRODAMOL™ CAP (Croda)) and isopropyl myristate (e.g. Tegosoft M (Evonik)) as well as silicone oils (e.g dimethicone (DW 200/100 (Dow Corning)).

The mascara composition of this invention may furthermore contain a film forming resin in an amount of 0.2 to 10 wt.-% based on the total weight of the composition. Particular suitable film forming resins include polyvinyl alcohol, polyvinyl acetate, PVP (e.g. PVP K-90 from Akzo), ammonium acrylates copolymer, cellulose gum (e.g. Tylose CG 200 (SE Tylose)); carboxymethyl hydroxyethylcellulose (e.g. Natrosol (Aqualon)), acrylate/ammonium methacrylate copolymers and acrylic/acrylate copolymers.

Particularly suitable inorganic coloring agents for the mascara compositions according to the present invention to the present invention are the iron oxides listed in the Color Index under reference CI 77499 such as Unipure Black LC989 from Sensient. Further suitable iron oxides for the mascara compositions according to the present invention are black, yellow, red and brown iron oxides listed in Color Index under references CI 77499, 77492 and 77491 such as Unipure RED LC381 from Sensient.

Particularly suitable inorganic coloring agents for foundation and/or make-up compositions according to the present invention include optionally surface treated titanium dioxides (rutile or anatase) listed in the Color Index under reference CI 77891 such as UNIPURE LC 981 AS-EM from Sensient. Further suitable inorganic coloring agents for foundation and/or make-up compositions according to the present invention include black, yellow, red and brown iron oxides, optionally surface treated, listed in the Color Index under references CI 77499, 77492 and 77491 such as Unipure RED LC381 from Sensient.

The compositions according to the invention in general have a pH in the range of 3 to 10, preferably a pH in the range of 4 to 8 and most preferably a pH in the range of 4 to 7.5. The pH can easily be adjusted as desired with suitable acids, such as e.g. citric acid, or bases, such as sodium hydroxide (e.g. as aqueous solution), triethanolamine (TEA Care), Tromethamine (Trizma Base) and Aminomethyl Propanol (AMP-Ultra PC 2000), according to standard methods in the art.

The following examples are provided to further illustrate the compositions and effects of the present invention. These examples are illustrative only and are not intended to limit the scope of the invention in any way.

EXAMPLES

A: Preparation of a Chlorine Free Cetyl Phosphate Surfactant Mixture According to the Present Invention 0.09 mol of cetyl alcohol is added into a flask and diluted with 20 ml of cyclohexane and heated to 75° C. Afterwards 0.3 mol of pyrophosphoric acid diluted in 30 ml of cyclohexane is slowly added. After the addition is complete the reaction is stirred for another hour at 75° C. Afterwards water is added and the reaction stirred for 15 min at 70° C. Then the water phase is separated and the organic phase is washed twice with water followed by removal of cyclohexane in vacuo. The thus obtained crude product is neutralised with 10 g of 50% KOH in water at 50° C. Then methanol is added and the crystallized product is filtered off. The resulting product is recrystallized from methanol resulting in 10 g of a cetyl phosphate surfactant mixture according to the present invention (corresponding to Amphisol® L).

1. Analytics 1. 1. Method for the Determination of Monocetylphosphate by Titration 1.5 g (+/−0.1 g) of the respective homogenized potassium cetylphosphate (powder) was weighed into a 150 mL Erlenmeyer flask with stopper. 60 mL of isopropanol/water mixture (20/80, v/v) was added. The suspension was stirred at 80° C. for 30 min in a closed flask. The solution was titrated at 70° C. on a heatable magnetic stirrer using 0.5 M sodium hydroxide solution as titrant.

1.2. Method for the Determination of Monocetylphosphate and Cetylalcohol by GC-FID 3-4 mg (+/−0.01 mg) of the respective homogenized potassium cetylphosphate (powder) was weighted into a 2 mL GC-Vial. 1 mL of a solution prepared by dissolving 140 mg tricosane (internal standard) in a 200 ml flask in 100 mL N,O-bis(trimethylsilyl)-trifluoroacetamide with 1% trimethylchlorosilane and pyridine (to 200 ml volume)) was added. The GC vial was closed and vortexed for 10 sec, followed by heating the vial for 20 min at 120° C. and vortexing the hot GC vial for another 10 sec. After cooling to RT, the samples were subjected to GC analysis in triplicates. (Column: Optima 5 HT, 30 m×0.25 mm 0.1 µm, Hydrogen flow rate: 2.2 mL/min (constant flow), Oven programme: 200° C. (0 min) Ramp to 360° C. (20° C./min), 360° C. (0 min)).

1.3. Method for the Determination of Dicetylphosphate by FIA-MS 100 mg (+/−0.01 mg) of the respective homogenized potassium cetylphosphate (powder) was weighted into a 100.0 ml glass volumetric flask. Then, 50.0 ml of tetrahydrofuran/water (70/30, v/v) was added and the mixture was sonicated for dissolution. The volume was adjusted with tetrahydrofuran/water (70/30, v/v). Then, 1 ml of this solution was diluted with an ammonium carbonate solution (300 mg ammonium carbonate in 100 ml water and 900 ml methanol) to 100 ml. Afterwards the amount of dicetyl phosphate was analyzed by FIA-MS (HPLC-MS Agilent 1260, No column, T=40° C., 5 µl, Detector: ESI-MS)

The amount of dicetyl phosphate in the sample was calculated using an external calibration with dicetyl phosphate.

1.3. Method for the Determination of Inorganic Phosphate 0.25 g of the respective homogenized potassium cetylphosphate was weighed into a 100 mL volumetric flask. After the addition of 90 mL THF/Water (70/30, v/v) the flask was placed in an ultrasonic bath for dissolution. Afterwards, the flask was filled to volume with THF/Water (70/30, v/v). 1 mL of this solution was pipetted into a 10 mL flask and filled up to volume with demineralised water. The samples were then analyzed in triplicates by IC chrompatography (Dionex ICS-3000, Chromatographic data system: Chromeleon, Detector: CD-3000 conductivity detector, Column: AS19 column (4.0 mm×250 mm) protected with an AG19 precolumn (4.0 mm×50 mm), Eluent: KOH gradient (0-55 mmol), injection volume 25 µl).

TABLE 1

Analytical results of various chlorine-free potassium cetyl phosphate surfactant mixtures

| Sample | Inv | Ref-1 | Ref-2 | Ref-3 |
|---|---|---|---|---|
| Monocetyl phosphate (wt.-%) | 75# | 79.6# | 47* | 73.6# |
| Dicetyl phosphate wt.-(%) | 6.8 | 10.1 | 11 | 22.5 |
| Inorganic phosphate (wt.-%) | 0.34 | 2.12 | 16.78 | 0.54 |
| Cetylalcohol (wt.-%) | 9.1 | 0.5 | 6.1 | 1.7 |
| heavy metals sum ppm | 8.0 | 12.1 | 23.1 | 23.0 | via Titration;
*via GC-FID (potassium cetyl phosphate surfactant mixtures: Inv: Amphisol ® L, Ref-1: EverMap 160K by Sino Lion, Ref-2: Crodafos MCK by Croda, Ref-3: Romol AFSK by Suzhou Eleco Chemical Industry Co. Ltd)

2. Formulation

The formulations as outlined in table 2 to 4 were prepared using the different potassium cetyl phosphate surfactant mixtures outlined in table 1. After storage at 22° C. for 6 weeks, respectively 3 months, the respective samples were assessed visually for their appearance. After 3 months additionally, the viscosity was measured for still intact samples using a Rheometer AR550 with plate SST ST 40 mm shear stress 10/s. As can be retrieved from the results outlined in table 2 to 4, only the formulations comprising the cetyl phosphate surfactant mixture according to the present invention led to stable formulations with an acceptable viscosity for the respective product form.

TABLE 2

Sunscreens (I) comprising different cetyl phosphate surfactant mixtures acc. to table 1

| | INCI/Name | Inv | Ref-1 | Ref-2 | Ref-3 |
|---|---|---|---|---|---|
| A | Cetearyl Alcohol | 2.30 | 2.30 | 2.30 | 2.30 |
| | Capric/Caprylic Triglycerides | 17.50 | 17.50 | 17.50 | 17.50 |
| | Diisopropylsebacate | 17.50 | 17.50 | 17.50 | 17.50 |
| | Titanium Dioxide & Silica & Dimethicone (PARSOL TX) | 6.00 | 6.00 | 6.00 | 6.00 |
| B | Aqua | Ad 100 | Ad 100 | Ad 100 | Ad 100 |
| | Potassium Cetyl Phosphate | 2.00 | 2.00 | 2.00 | 2.00 |
| C | Phenoxyethanol & Ethylhexylglycerin | 1.00 | 1.00 | 1.00 | 1.00 |
| | Viscosity (mPas) after 12 weeks | 4200 | 32640 | 33220 | Phase separation (6 weeks) |

TABLE 3

Sunscreens (II) comprising different potassium cetyl phosphate surfactant mixtures acc. to table 1

| | INCI/Name | Inv | Ref-1 | Ref-2 | Ref-3 |
|---|---|---|---|---|---|
| A | Cetearyl Alcohol | 2.30 | 2.30 | 2.30 | 2.30 |
| | Capric/Caprylic Triglycerides | 17.50 | 17.50 | 17.50 | 17.50 |
| | Diisopropylsebacate | 17.50 | 17.50 | 17.50 | 17.50 |
| | Titanium Dioxide & Silica & Dimethicone (PARSOL TX) | 8.00 | 8.00 | 8.00 | 8.00 |
| B | Aqua | Ad 100 | Ad 100 | Ad 100 | Ad 100 |
| | Potassium Cetyl Phosphate | 2.00 | 2.00 | 2.00 | 2.00 |
| C | Phenoxyethanol & Ethylhexylglycerin | 1.00 | 1.00 | 1.00 | 1.00 |
| | Viscosity (mPas) after 12 weeks | 6440 | 21440 | 32120 | Phase separation (12 weeks) |

TABLE 4

Foundations comprising different potassium cetyl phosphate surfactant mixtures acc. to table 1

| | INCI/Name | Inv | Ref-1 | Ref-2 | Ref-3 |
|---|---|---|---|---|---|
| A | Cetyl Alcohol | 2.00 | 2.00 | 2.00 | 2.00 |
| | Paraffinum Liquidum | 14.00 | 14.00 | 14.00 | 14.00 |
| | *Euphorbia Cerifera* (Candelilla) Wax | 3.40 | 3.40 | 3.40 | 3.40 |
| | Cera Alba | 4.40 | 4.40 | 4.40 | 4.40 |
| | Potassium Cetyl Phophate | 8.00 | 8.00 | 8.00 | 8.00 |
| | Steareth-21 | 0.50 | 0.50 | 0.50 | 0.50 |
| | CI 77891 (and) Triethoxycaprylylsilane (Unipure White LC 981 AS-EM) | 10.00 | 10.00 | 10.00 | 10.00 |
| C | Aqua | Ad 100 | Ad 100 | Ad 100 | Ad 100 |
| | Glycerin | 2.00 | 2.00 | 2.00 | 2.00 |
| | Hydroxyethylcellulose | 0.50 | 0.50 | 0.50 | 0.50 |
| | *ACACIA* SENEGAL GUM | 3.00 | 3.00 | 3.00 | 3.00 |

TABLE 4-continued

Foundations comprising different potassium cetyl phosphate surfactant mixtures acc. to table 1

| INCI/Name | Inv | Ref-1 | Ref-2 | Ref-3 |
|---|---|---|---|---|
| D PEG/PPG-18/18 Dimethicone | 0.50 | 0.50 | 0.50 | 0.50 |
| Dimethicone | 0.50 | 0.50 | 0.50 | 0.50 |
| Phenoxyethanol & Ethylhexylglycerin | 0.70 | 0.70 | 0.70 | 0.70 |
| Viscosity (mPas) after 12 weeks | 36440 | 56850 | 49110 | 48160 |

TABLE 5

Mascara comprising different potassium cetyl phosphate surfactant mixtures acc. to table 1

| | INCI/Name | Inv | Ref-2 | Ref-3 |
|---|---|---|---|---|
| A | Cetyl Alcohol | 2.00 | 2.00 | 2.00 |
| | Paraffinum Liquidum | 14.00 | 14.00 | 14.00 |
| | *Euphorbia Cerifera* (Candelilla) Wax | 3.40 | 3.40 | 3.40 |
| | Cera Alba | 4.40 | 4.40 | 4.40 |
| | Potassium Cetyl Phophate | 8.00 | 8.00 | 8.00 |
| | Steareth-21 | 0.50 | 0.50 | 0.50 |
| | Iron Oxides (Unipure Black LC989) | 10.00 | 10.00 | 10.00 |
| C | Aqua | Ad 100 | Ad 100 | Ad 100 |
| | Glycerin | 2.00 | 2.00 | 2.00 |
| | Hydroxyethylcellulose | 0.50 | 0.50 | 0.50 |
| | *ACACIA* SENEGAL GUM | 3.00 | 3.00 | 3.00 |
| D | PEG/PPG-18/18 Dimethicone | 0.50 | 0.50 | 0.50 |
| | Dimethicone | 0.50 | 0.50 | 0.50 |
| | Phenoxyethanol & Ethylhexylglycerin | 0.70 | 0.70 | 0.70 |
| | Viscosity (mPas) after 12 weeks | 38240 | 64510 | 47800 |

The invention claimed is:

1. A topical composition comprising:
at least one inorganic micropigment, and
a cetyl phosphate surfactant mixture consisting essentially of, based on total weight of the surfactant mixture:
(i) 60-95 wt. % of monocetyl phosphoric acid or a salt thereof,
(ii) 0-15 wt. % of dicetyl phosphoric acid or a salt thereof,
(iii) 0-20 wt. % of cetyl alcohol,
(iv) 0-0.7 wt. % of an inorganic phosphate,
(v) 0-12 ppm of heavy metals, and
(vi) 0-4 wt. % of residual water, wherein the surfactant mixture contains no organochlorine impurities.

2. The topical composition according to claim 1, wherein the salts of the monocetyl phosphoric acid and the dicetyl phosphoric acid are potassium salts thereof.

3. The topical composition according to claim 2, wherein the cetyl phosphate surfactant mixture is a potassium cetyl phosphate surfactant mixture consisting essentially of:
(i) 72-85 wt.-% of the monocetyl phosphate,
(ii) 0.5-10 wt.-% of the dicetyl phosphate,
(iii) 0-15 wt.-% of the cetyl alcohol,
(iv) 0-0.6 wt.-% of the inorganic phosphate,
(v) 0-11 ppm of the heavy metals
(vi) 0-2.5 wt. % of the residual water, and
(vii) 7-12 wt. % of potassium.

4. The topical composition according to claim 1, wherein the cetyl phosphate surfactant mixture is present in an amount of 0.1 to 10 wt. %, based on total weight of the topical composition.

5. The topical composition according to claim 1, wherein the cetyl phosphate surfactant mixture is present in an amount of 0.3 to 8 wt. %, based on total weight of the topical composition.

6. The topical composition according to claim 1, wherein the cetyl phosphate surfactant mixture is present in an amount of 0.5 to 8 wt. %, based on total weight of the topical composition.

7. The topical composition according to claim 1, wherein the inorganic micropigment is present in an amount selected in the range of 0.1 to 40 wt.-%, based on the total weight of the composition.

8. The topical composition according to claim 1, wherein
the monocetyl phosphoric acid or a salt thereof is present in an amount of 70-90 wt. %,
the dicetyl phosphoric acid or a salt thereof is present in an amount of 0.5-12 wt. %, and
the residual water is present in an amount of 0-3 wt. %.

9. The topical composition according to claim 1, wherein the inorganic micropigment is an inorganic sunscreening agent or a coloring agent.

10. The topical composition according to claim 9, wherein the inorganic sunscreening agent is a titanium dioxide having an average primary particle size in a range of about 2 nm to 100 nm, and a secondary particle size in a range of about 0.05 to 50 μm.

11. The topical composition according to claim 10, wherein the titanium dioxide is a double coated titanium dioxide having an inner inorganic silica coating and an outer organic coating selected from the group consisting of simethicone, methicone, dimethicone, polysilicone-15, stearic acid and mixtures thereof.

12. The topical composition according to claim 9, wherein the coloring agent is an iron oxide or a titanium dioxide having a particle size in a range of 0.001 to 150 μm.

13. The topical composition according to claim 12, wherein the particle size of the coloring agent is in a range of 0.002 to 100 μm.

14. The topical composition according to claim 12, wherein the particle size of the coloring agent is in a range of 0.02 to 50 μm.

15. The topical composition according to claim 1, wherein the topical composition is an oil-in-water (O/W) emulsion comprising an oily phase dispersed in an aqueous phase.

16. The topical composition according to claim 15, wherein the composition is a sunscreen, a mascara or a makeup/foundation composition.

* * * * *